United States Patent [19]

Paloheimo

[11] Patent Number: 5,482,035
[45] Date of Patent: Jan. 9, 1996

[54] METHOD FOR MONITORING THE CONDITION OF A PATIENT

[75] Inventor: Markku Paloheimo, Helsinki, Finland

[73] Assignee: Instrumentarium Corporation, Finland

[21] Appl. No.: 214,641

[22] Filed: Mar. 17, 1994

[30] Foreign Application Priority Data

Mar. 19, 1993 [FI] Finland .................................... 931234

[51] Int. Cl.$^6$ ........................................................ A61B 5/00
[52] U.S. Cl. ............................................ 128/630; 128/898
[58] Field of Search ...................................... 128/630, 898

[56] References Cited

U.S. PATENT DOCUMENTS

| | | |
|---|---|---|
| 3,814,082 | 6/1974 | Taylor . |
| 4,197,854 | 4/1980 | Kasa . |
| 4,595,015 | 6/1986 | Jansen et al. . |
| 4,967,754 | 11/1990 | Rossi . |
| 5,018,067 | 5/1991 | Mohlenbrock et al. . |

FOREIGN PATENT DOCUMENTS

| | | |
|---|---|---|
| 135134 | 3/1985 | European Pat. Off. . |
| 269907 | 6/1988 | European Pat. Off. . |
| 347345 | 12/1989 | European Pat. Off. . |

*Primary Examiner*—Angela D. Sykes
*Assistant Examiner*—Stephen Huang
*Attorney, Agent, or Firm*—Andrus, Sceales, Starke & Sawall

[57] ABSTRACT

The invention relates to a method for anticipating a change occurring in the condition of a patient's organism before the condition of a patient reaches a critical point, the condition of a patient's organism being monitored by the application of an appropriate measuring method and the determinations according to said measuring method being effected at appropriate time intervals. The measuring results obtained on the basis of effected measurements, the number of which must be at least two, or quantities derived therefrom are utilized for predicting the future development of one or more measuring results and, if a measuring result according to the prediction indicates that a limit value representing a predetermined critical point is reached in the condition of a patient within a predetermined period of time, a warning signal is released indicating that this critical point is being approached.

17 Claims, 3 Drawing Sheets

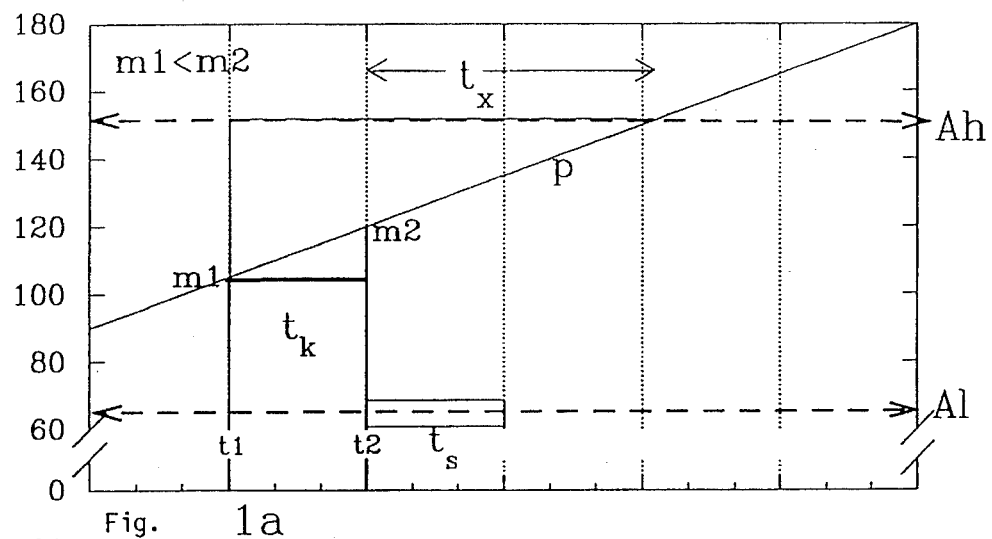
Fig. 1a
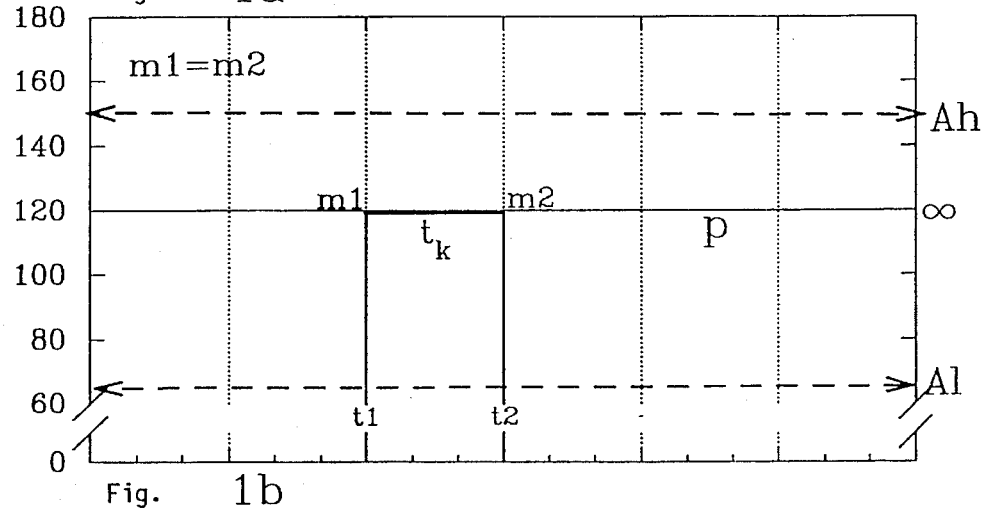
Fig. 1b
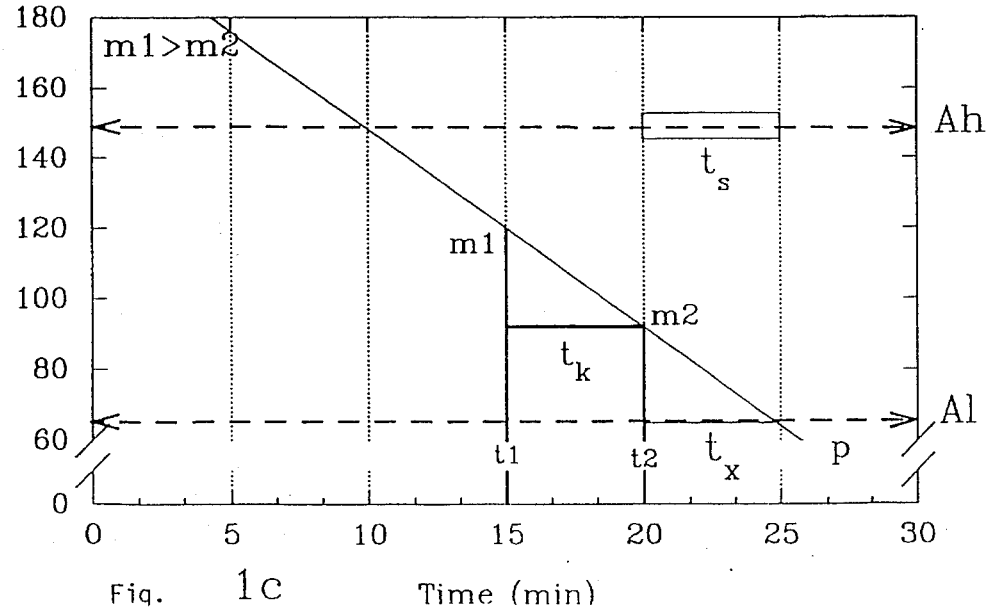
Fig. 1c   Time (min)

1

METHOD FOR MONITORING THE CONDITION OF A PATIENT

BACKGROUND OF INVENTION

The present invention relates to a method for anticipating a change occurring in the condition of a patient's organism before the condition of a patient reaches a critical point, the condition of a patient's organism being monitored by the application of an appropriate measuring method and the determinations according to said measuring method being effected at appropriate time intervals.

In the monitoring of all types of phenomena it is usual that the variables subjected to monitoring be set with upper and lower limit values, the breaking of which produces a report. Such a report is also often referred to as an alarm. Momentary signal faults unrelated to the specific character of a quantity being monitored produce needless reports. Efforts have been made to eliminate needless and monitor-interfering reports by filtering the basic quantities in various ways and by delaying a report to be issued. The result of both filtering and delaying is a late appearance of a report received on a "legitimate" occurrence relative to the occurrence itself and even an alarm that is too late from the clinical point of view.

The reporting sensitivity can be regulated by the location of limit values in relation to the normal behaviour of a signal; a narrow limit value range produces more readily reports about deviations from the normal range while a wide limit value range may leave substantial changes unnoticed. The reporting philosophy based solely on a limit value range does not take the rate of changes into consideration. Even in the best of circumstances, the reporting system based en a limit value produces plenty of false alarms, the occurrence of which causes a temptation to either widen the limit value range or to switch off the alarm system.

If the normal value of a variable being monitored fluctuates between situations and individual, the fixed limit values must have a sufficiently wide range to include the entire natural fluctuation range for a quantity being monitored. Efforts have been made to enhance the reporting sensitivity by using automatic limit values, which are relatively narrow and which are set on either side of a standardized variable an a "suitable" distance according to sensible arguments. In the systems, the basic distances or ranges for automatic reports cannot be generally changed by the operator since the automatically set limit values indicate more sensitively the deviations of a quantity from a normal value, the use thereof often causes "needless" reports and is a temptation towards the adoption of fixed, wider limit values.

The behaviour of one variable can be anticipated if the pharmaco-kinetic and pharmaco-dynamic properties of pharmaceuticals having an effect thereon are known and mathematical patterns are used for calculating the dosage based effects on quantities being measured (Jan J. van der Aa JJ, Betoken JEW, van Oostrom JH, Gravenstein JS: Integration concepts for anesthesia workstation displays, J Clin Monit 1992; 8:51–2). This so-called projection technique is not based on observations but, instead, on expert systems which, on the other hand, are based on generalized allegations and experimentally discovered mathematical quantities.

SUMMARY OF INVENTION

An object of this invention is to eliminate the above problems. Thus, an object of the invention is to provide a method that can be used for anticipating a change occurring in the condition of a patient. Another object of the invention is to provide a method that can be used for informing the operator of the fact that a variable representing the condition of a patient is showing a shift towards a limit value indicating the critical condition. A yet further object of the invention is to provide a method that can be applied by using already existing limit values as a framework for the grounds of reporting in a manner that the operator will be cautioned if the variable will, judged on the basis of the present behaviour, soon break a limit value. A particular object is to provide a method which, on the basis of detected values obtained from some variable preferably at equal intervals, can be used for pre-warning that, within a certain period of time, said variable will break a limit value set above and/or below the normal fluctuation range of the variable.

The characterizing features for a method of the invention are set forth in the annexed claims.

The invention relates to a method that can be used for predicting a change occurring in the condition of a patient's organism. The inventive method involves the application of a measuring method or technique that can be used for monitoring the condition of and changes occurring in an organism. In the inventive method, the measuring results obtained on the basis of two or more measurements are utilized for the determination of a change occurring in the condition of a patient. If, on the basis of the change, it can be concluded that a predetermined limit value indicating the critical condition of a patient will be reached within the lapse of some predetermined period of time, a warning will be given prior to reaching this limit value.

Thus, the method can be used for monitoring the variation rate of measuring results based on the effected measurements. The method involves some inherent automatics, such that the reporting sensitivity increases as the variable is approaching a limit value. A method of the invention is applicable in patient surveillance monitors capable of monitoring e.g., the condition of a patient in anesthesia. There may be simultaneously a plurality of measuring quantities to be monitored. A need for the early detection of rapid, unfavourable changes concerns particularly measuring quantities relating to blood circulation and respiration, such as pulse rate, systolic blood pressure, partial oxygen pressure of a respiratory gas, oxygen saturation of arterial blood, concentration of an anesthetic gas or even electrical phenomena of the central nervous system.

The computation applicable to the method can be carried cut e.g. by means of generally applied statistical forecasting methods on the basis of the data or components thereof included within an observation time lapse or trigonometrically by using e.g. the last two measuring values or the average values of the two halves of an observation time lapse. The computation may be accompanied by moderately filtering or softening the material without causing the delay of a warning signal. The warning signals can be conditioned in a manner that, if the noise of a measuring result exceeds certain limits, there will only be a report about the noise or the latest noise-free value will be reported accompanied by a comment that the warning signal procedure is impossible due to noise for informing the operator of the fact that an anticipatory warning cannot be given.

The operator of a patient monitor, said monitor thus employing a method of the invention, is capable of influencing the sensitivity of a warning signal in the method in three ways: First of all, by determining the number of observations serving as the ground for computation, the durations of an observation time lapse or observation periods; secondly, by setting the limit values; and thirdly, by setting the time lapse tolerated thereby, after the expiry of which a variable at a certain varying rate would be allowed to break the set limit value without a consequential report and, if a variable at a certain varying rate should break the set limit value within this time lapse, a report would result.

These regulators facilitate a versatile configuration in relation to each parameter in a manner than an operator familiar with the method receives an advance warning about an incoming alarm and can react to a change that has produced the warning even prior to the alarm. By adjusting the warning time lapse to zero, the anticipatory warning system can be transformed even for each parameter into a conventional limit value alarm system.

The invention will now be described in more detail with reference made to the accompanying patent drawings, in which

BRIEF DESCRIPTION OF DRAWINGS

FIGS. 1a, 1b and 1c illustrate measuring results of one variable performed on a patient and one trigonometric solution of time lapses as well as an inventive utilization of these measuring results, FIGS. 3a and 3b illustrates results obtained from one pulse rate measuring process, the measurements being effected on a patient continuously and averaged at certain (10 s) time intervals, and an inventive utilization based on the set of measuring results.

DETAILED DESCRIPTION

Figure 2A:
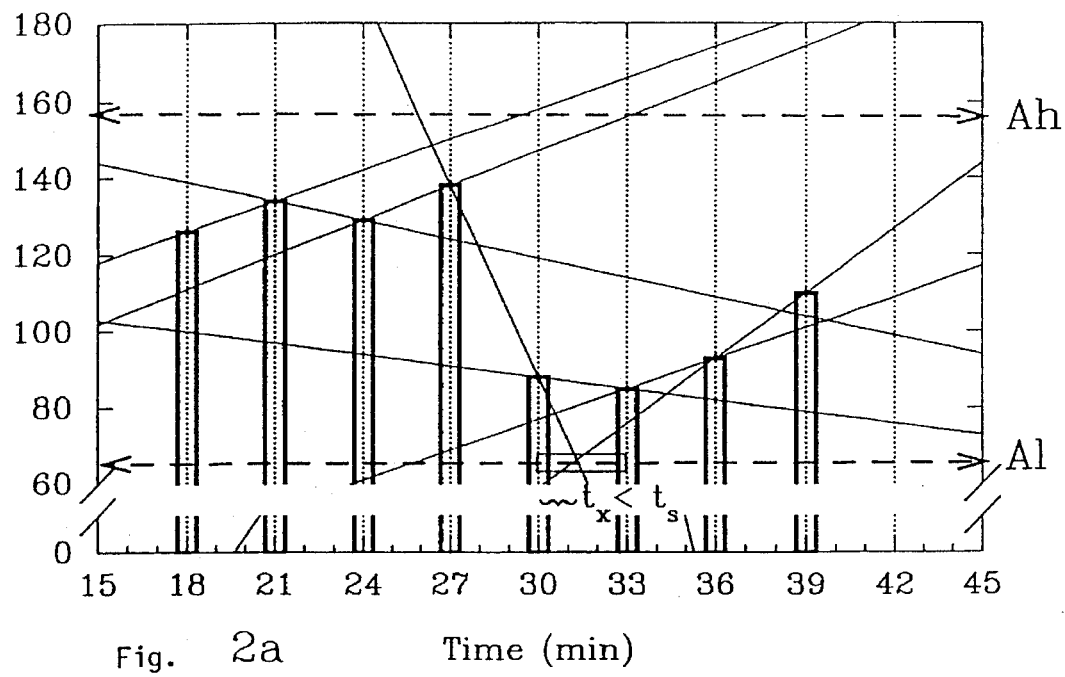
FIGS. 2a and 2b illustrate results obtained from one blood pressure measuring process, the measurements being effected on a patient continuously at certain time intervals, and an inventive utilization of the measuring results.

The following definitions deal with some of the terms appearing in the specification:

Prediction time (tx) is the time forward from the latest observation after which a measuring result, on the basis of previously made observations, would break a limit value indicating the critical point provided that the current varying rate is maintained.

Measuring result (m) is a numerical quantity obtained on the basis of a measurement and determined in relation to time.

Alarm is a signal which is produced as the measuring result has reached a set limit value. The alarm is preferably a sound signal determined by the international standards (International standardization Organization, ISO and Comité Européen de Normalisation, CEN), which may be accompanied by a visually detectable signal.

Pointer (p) is a prediction made for one or more upcoming measuring results on the basis of at least two measuring results or on the basis of measuring results having appeared during at least two measuring cycles. Particularly, the pointer is a temporally forward extending straight line defined mathematically on the basis of the measured quantities or the averages thereof.

Limit value is a numerical quantity level, determined by the operator and higher (Ah, upper limit) or lower (Al, lower limit) than a normally occurring measuring result, the reaching or breaking /of which produces an alarm.

Limit value range is a fluctuation range measuring results between the limit values.

Tolerance time (ts) is a time period for warning the operator if, during this time period, a predetermined limit value indicating the critical condition of a patient is reached.

FIG. 1 discloses the grounds for calculation useful in a method of the invention: A time lapse between two successive blood pressure measurements is tk. Through measuring results m1 and m2 is extended a pointer p which meets with a limit value Ah (alarm high) after the time tk from the latter measurement. The pointer p is a straight line and its extrapolation can be effected trigonometrically:

The expressions $$tx1=(Al-m2)*tk/(m2-m1)$$

and $$tx2=(Ah-m2)*tk/(m2-m1)$$

are provided with Al (=lower limit value), Ah (=higher limit value), m1 (=first measuring result), m2 (=latter measuring result) and tk (=time lapse between the measurements, t2−t1), the positive value of tk being a prediction time. Also other trigonometrical calculation methods are possible. In the most simple case, the measuring interval tk may be equal to the tolerance time ts determined by the operator or a multiple (n*ts) thereof.

It should be noted that the quantities Ah, Al m1 and m2 are measured on the same scale and are of a common type while tk, ts and tx refer to time.

In FIG. 1a, the pointer p meets the higher limit Ah in time tx calculated from measuring moment t2; it is confirmed that tx>ts, resulting in no report. In FIG. 1c, respectively, the pointer p meets the lower limit Al in time tx calculated from measuring moment t2; it is confirmed that tx<ts, resulting in a report about the fact that, at the verified varying rate, the alarm limit Al will be reached within time period ts. FIG. 1b shows a special case, wherein m1=m2 and, thus, tx assumes no value.

FIG. 1 may be an example of automatic blood pressure measurement, which typically produces one value from a measurement effected at regular intervals. Clinically, it would be sensible that the duration of ts be set equal to that of measuring interval tk for producing a report in cases that the measurement value at the verified rate would descend below an alarm value prior to effecting the following measurement.

Figure 2B:
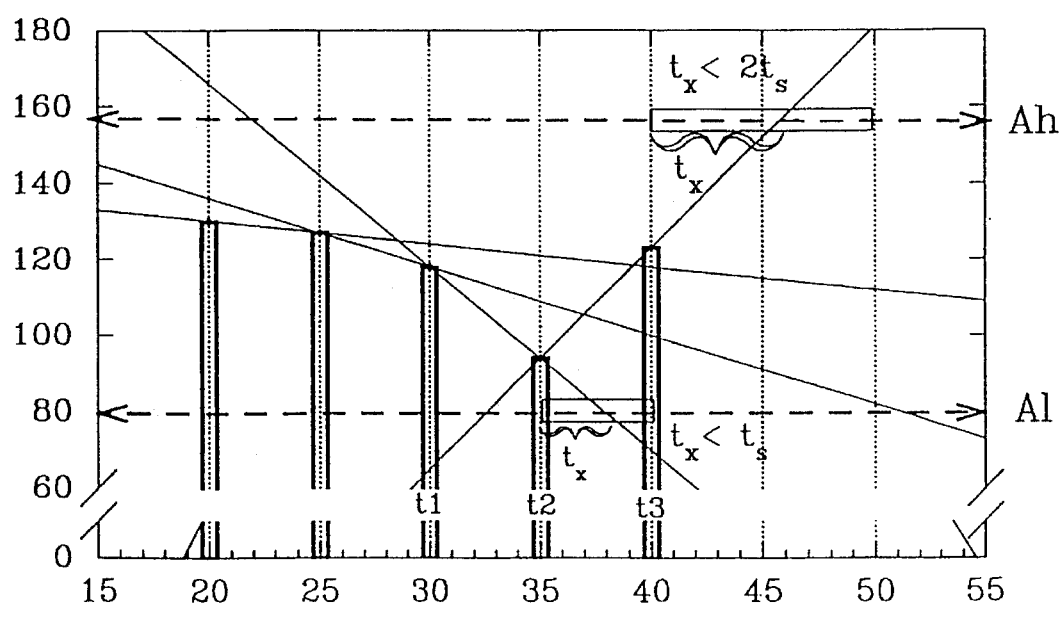

FIG. 2 illustrates a plurality of successive measurements. FIG. 2a shows an example, wherein measurements are effected at three-minute intervals while the example of FIG. 2b shows measurements effected at five-minute intervals. FIG. 2a shows at 30 minutes such a major drop of blood pressure that tx<ts, resulting in a warning report. Thus, in this exemplary case, ts is 3 minutes i.e. equal to the measuring interval. It could be concluded from the figure that the warning has led to actions, which have resulted in the re-rise of blood pressure. Pig. 2b illustrates a similar situation over the time lapse t1–t2. The lower alarm limit has a tolerance time ts of five minutes, i.e. equal to the measuring interval. The operator has set the tolerance time of a higher alarm limit to be twice as long and the figure shows a situation, wherein the varying rate over a time lapse t2–t3 produces a report and, thus, the operator can conclude on the basis of the figure that the blood pressure has returned in the manner and at the speed of his or her desire.

It is a common practice to show frequently occurring quantities as an average obtained over certain time lapses or calculated on the basis of a certain set of measuring results. FIG. 3a discloses averages (circles) of heart rates measured over 10 seconds. Within two successive measuring cycles of thirty seconds there are three+three average figures. In FIG.

3a, there is calculated three pointers p1, p2 and p3, the last of which is based on observation cycles (boxes) having medians (m1 and m2) with the pointer p3 extending therethrough. It is confirmed that p1 and p2 reach the limit value Al so far away that no report is given. Instead, the pointer p3 meets the limit value Al within time ts, resulting in is report. Clinically, it can be seen on the basis of the figure that the operator has undertaken actions for bringing the pulse rate to a normal level prior to receiving a limit value alarm, The pointers of FIG. 3 could also be determined by the application of linear regression calculation for example to the last six observation values and by solving the moment at which the regression straight crosses the limit value levels.

In anticipation, the location of a pointer is temporally defined in the middle of the applied measuring cycles (at the averages). Depending on the nature of any given quantity and on the need of anticipating its behaviour, the averages can be temporally shifted to the forward edge of measuring cycle, the location of a pointer shifting respectively forward. As for some measuring quantities, the delay of a report resulting therefrom may be appropriate.

Figure 3B:
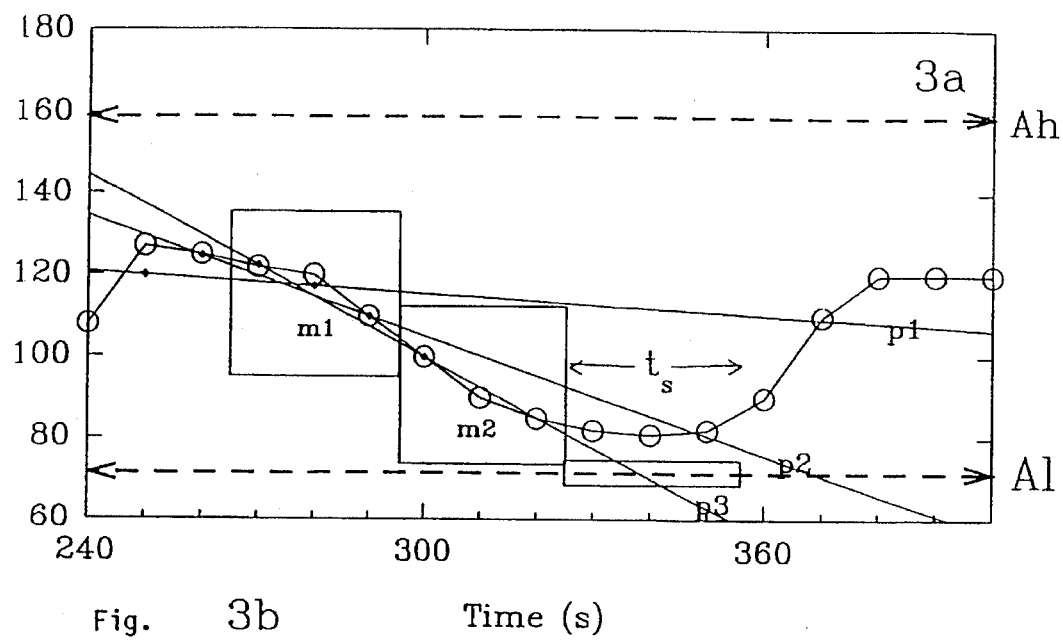
Figure 3B:
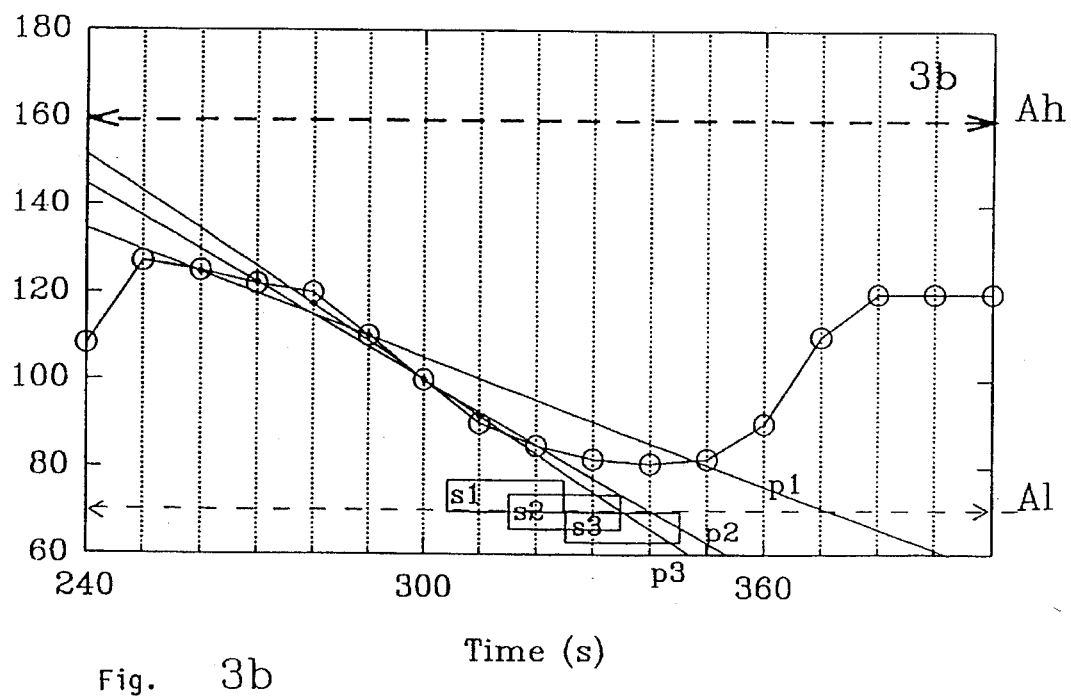

FIG. 3b illustrates the increase of reporting sensitivity when approaching a limit value. The pointers p1 and p2 do not find themselves within timed s1 and s2 but the pointer p3 his the limit value Al within time s3, although the pointer has a slope which is nearly equal to that of pointer p2; the proximity of a limit value has sensitized the release of a report.

Shifting the limit values Ah and Al further away from the normal fluctuation range of a quantity results in desensitization of an anticipatory warning; this requires a steeper regression slope or a more intensive change for reaching a tolerance time on the other hand, bringing the limit values closer sensitizes the release of an anticipatory warning. The easy operation of the method requires simple technique of shifting the limit values Ah and Al.

A change in the duration of a tolerance time also affects the occurring sensitivity of a warning: A long tolerance time is more sensitive to release warnings than a short one. The tolerance time should be capable of being adjusted separately in terms of each quantity to be measured; each measuring quantity should be provided with a tolerance time characteristic thereof.

The adjustment of a tolerance time to zero switches off the anticipatory warning device as far as that particular measuring quantity is concerned. According to general alarming principles, a program can be used for inactivating the anticipatory warning device as far as either a warning sound or a possible visible report is concerned.

The tolerance time can be divided in two sections, whereof the latter would produce a reminder and the former a more serious warning.

In medical monitoring, it would be beneficial if a quantity could be detected to change unusually rapidly before it reaches a set alarm limit value. Time will be gained if treatment procedures can be started before a particular variable has reached a value which the operator has considered unnecessary low or high.

The invention is by no means limited to the above-described embodiments but various details of the invention can be modified within the scope off the claims.

The anticipatory warning process could also be applied in other fields that require fast actions, such as process engineering, aviation, and traffic engineering in general. A suitable feedback could be used for softening the counteractions, if it is possible to respond to a changing rate and non just to limit values.

I claim:

1. A method for monitoring a patient and anticipating a change occurring in a condition of a patient's organism before the condition of a patient reaches a critical point, said method comprising the steps of:

monitoring and measuring at least one patient characteristic at specified time intervals to create a series of characteristic signals indicative of a condition of the patient's organism;

applying a computational measuring method to at least two of the characteristic signals thereby creating at least one measuring result signal;

determining, according to the measuring result signal a change occurring in the condition of the patient;

predicting a future condition of the patient's organism based on the change in the condition of the patient;

setting a limit value representing a predetermined critical point in the condition of the patient;

setting a predetermined period of time in which it is desired to track a future condition with respect to the limit value; and generating a warning signal if a predicted future condition indicates that the limit value representing a predetermined critical point will be reached within the predetermined period of time, thereby indicating that the critical point is being approached by the monitored and measured patient characteristic thereby permitting preventive treatment to the patient.

2. A method as set forth in claim 1, characterized in that the limit value representing the critical point is further defined as a higher and/or lower limit value than an acceptable numerical quantity level of the monitored patient characteristic.

3. A method as set forth in claim 1, characterized in that the warning signal is generated when the measuring result signal representing the condition of a patient breaks the limit value representing the critical point.

4. A method as set forth in claim 1, characterized in that the predicting of a future condition is carried out on the basis of at least two measurements effected at different times, the measurements having been effected by the application of a common measuring method.

5. A method as set forth in claim 1, characterized in that the predicting of a future condition is carried out on the basis of at least two successive accepted measurements.

6. A method as set forth in claim 1, characterized in that the measuring result signals are arranged in at least two groups, each group having at least two measuring result signals, and the measuring result included in such a group are worked into one common measuring result signal representing such measuring result signals, the future condition of a measuring result signal being predicted on the basis of the measuring result signals representing the groups.

7. A method as set forth in claim 6, characterized in that the measuring result signals included in a group comprise the results of successive sequential accepted measuring processes.

8. A method as set forth in claim 4, characterized in that the predetermined period of time wherein the warning signal is generated indicating that the limit value representing the predetermined critical point in the condition of a patient is reached, is at least as long as a time between the effected measurements.

9. A method as set forth in claim 4, characterized in that the predetermined period of time wherein the warning signal is generated indicating that the limit value representing the predetermined critical point in the condition of a patient is reached, is at least as long as an added time lapse between measurements required for a group of measurements to be set up from the measuring result signals.

10. A method as set forth in claim 4, characterized in that the predetermined period of time wherein a warning signal is generated indicating that the limit value representing the predetermined critical point in the condition of a patient is reached, is calculated from such an effected measurement that a measuring result signal obtained therefrom is used when predicting the future condition of one or more measuring result signals.

11. A method as set forth in claim 4, characterized in that the predetermined period of time wherein a warning signal is generated indicating that the limit value representing the predetermined critical point in the condition of a patient is reached, is calculated from such a latest effected measurement that a measuring result signal obtained therefrom is used when predicting the future condition of one or more measuring result signals.

12. A method as set forth in claim 1 characterized in that the warning signal comprises a visible signal.

13. A method as set forth in claim 1 characterized in that the warning signal comprises a sound signal.

14. A method as set forth in claim 1 characterized in that the alarm signal comprises a visible signal.

15. A method as set forth in claim 2, characterized in that the warning signal is generated when the measuring result signal representing the condition of a patient breaks the limit value representing the critical point.

16. A method as set forth in claim 15, characterized in that the warning signal comprises a visible signal.

17. A method as set forth in claim 15, characterized in that the warning signal comprises a sound signal.

* * * * *